United States Patent
Pham et al.

(10) Patent No.: US 8,840,742 B2
(45) Date of Patent: Sep. 23, 2014

(54) SYSTEM AND METHOD OF DETECTING A MISSING TOW IN A COMPOSITE LAYUP

(71) Applicants: Truong D. Pham, Lynnwood, WA (US); Samuel Stewart, Redmond, WA (US)

(72) Inventors: Truong D. Pham, Lynnwood, WA (US); Samuel Stewart, Redmond, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/671,552

(22) Filed: Nov. 7, 2012

(65) Prior Publication Data

US 2014/0124120 A1 May 8, 2014

(51) Int. Cl.
*B32B 41/00* (2006.01)
*B29C 70/38* (2006.01)
*G01N 25/72* (2006.01)

(52) U.S. Cl.
CPC ............. *B32B 41/00* (2013.01); *B29C 70/38* (2013.01); *G01N 25/72* (2013.01)
USPC ............. 156/64; 156/350; 156/359; 156/360; 156/362; 156/363; 156/378; 156/379

(58) Field of Classification Search
CPC .......... G01N 25/72; G01N 2021/8472; G01N 21/171; G06T 2207/10048; B29C 2037/903; B29C 35/0288; B29C 66/90; B29C 70/30
USPC ........... 156/64, 350, 359, 360, 362, 363, 378, 156/379
See application file for complete search history.

(56) References Cited

U.S. PATENT DOCUMENTS

| 5,166,789 | A | 11/1992 | Myrick |
| 5,266,139 | A | 11/1993 | Yokota et al. |
| 6,799,619 | B2 * | 10/2004 | Holmes et al. ................. 156/358 |
| 7,489,392 | B2 * | 2/2009 | Engelbart et al. .......... 356/237.1 |
| 7,513,964 | B2 | 4/2009 | Ritter et al. |
| 2002/0141632 | A1 | 10/2002 | Engelbart et al. |
| 2003/0169433 | A1 | 9/2003 | Koele et al. |
| 2005/0203657 | A1 * | 9/2005 | Engelbart et al. ............. 700/110 |
| 2006/0109454 | A1 | 5/2006 | Engelbart et al. |
| 2006/0191622 | A1 * | 8/2006 | Ritter et al. ..................... 156/64 |
| 2008/0055591 | A1 * | 3/2008 | Walton ....................... 356/237.1 |

FOREIGN PATENT DOCUMENTS

| EP | 1980847 | 10/2008 |
| EP | 2072224 | 6/2009 |

OTHER PUBLICATIONS

Ingersoll Machine Tools, On Tool Inspection of Automated Composite Material Placement, Jan. 18, 2012, http://ncdmm.org/wp-content/uploads/2013/01/Proposal_Ingersoll-Machine-Tools.pdf.*
PCT US2013063697 International Search Report dated Dec. 6, 2013.

* cited by examiner

*Primary Examiner* — Jeff Aftergut
*Assistant Examiner* — Joshel Rivera (57) ABSTRACT

A system for detecting a missing tow in a tow band may include a fiber placement head for applying a tow band to a substrate forming a composite layup. The system may further include a heating device for preheating the substrate prior to application of the tow band. The system may additionally include an infrared camera mounted to the fiber placement head and configured to generate a real-time thermal image of the composite layup during the application of the tow band to the substrate.

17 Claims, 6 Drawing Sheets

SYSTEM AND METHOD OF DETECTING A MISSING TOW IN A COMPOSITE LAYUP

FIELD

The present disclosure relates generally to composites manufacturing and, more particularly, to a system and method for detecting a missing tow in a composite layup.

BACKGROUND

Composite structures may be fabricated using automated fiber placement machines to apply continuous strips or bands of tows of pre-impregnated fibers onto a tool or mandrel to form a composite layup having a plurality of plies. Each tow may be comprised of several tow segments that may be spliced end-to-end using resin. The tows may be drawn from a plurality of tow spools that may be mounted on a fiber placement head. The fiber placement head may include a tow collimator for aligning the plurality of tows into side-by-side arrangement with one another to form a tow band. From the tow collimator, the tow band may be fed to an application device of the fiber placement head where the tow may be pressed onto the tool or mandrel as the fiber placement head moves along the tool following the contour of the tool surface.

Occasionally, during the process of applying a tow band to a tool surface, a tow may be missing from the tow band such as due to a misfeed of a tow though the collimator or through other components of the fiber placement head. A tow may also be missing due to a break in a splice of the tow. In addition, a tow may be missing due to the tow falling off of the tool surface after the tow is applied to the tool due to insufficient tack between the tow and tool surface or substrate.

Conventional methods of detecting missing tows include visual inspection of the composite layup for the presence of depressions in the layup surface which may be indicative of a missing tow. Unfortunately, detection of a depression in the layup surface may be difficult due to the relatively small thickness (e.g., 0.008 inch) and relatively small width (e.g., 0.125 inch) of each tow. In addition, the difficulty in detecting a depression in the layup surface by visual inspection with the human eye may be compounded when the composite layup is comprised of overlapping plies having tows with the same fiber orientation resulting in minimal contrast due to the black color of the tow. Tactile inspection of the layup surface may be impractical for the relatively large amount of surface area associated with certain composite structures. In addition, tactile inspection may not yield the desired results.

A further drawback associated with conventional methods for detecting missing tows is that the fiber placement machine may continue to apply composite material with a missing tow in a tow band. For example, multiple plies of composite material may be laid over an area with a missing tow before the missing tow is detected and the fiber placement machine is stopped. In order to rework the area of the composite layup with the missing tow, the general area of the missing tow may be generally identified. However, rework of the composite layup may require the removal and replacement of material in a labor-intensive process and time-consuming process at significant cost. Furthermore, because the area of the missing tow(s) is only generally known, large amounts of material may require removal before reaching the exact location of the missing tow.

As can be seen, there exists a need in the art for a system and method for detecting a missing tow in a composite layup with improved accuracy. In addition, there exists a need in the art for a system and method for detecting a missing tow in a composite layup wherein the exact location of the missing tow may be identified prior to minimize the amount of composite material that is removed during the rework process.

SUMMARY

The above-noted needs associated with detection of missing tow are specifically addressed and alleviated by the present disclosure which provides a system for detecting a missing tow in a tow band. The system may include a fiber placement head for applying a tow band to a substrate forming a composite layup. The system may further include a heating device for preheating the substrate prior to application of the tow band. The system may additionally include an infrared camera mounted to the fiber placement head and configured to generate a real-time thermal image of the composite layup during the application of the tow band to the substrate.

In a further embodiment, disclosed is a system for detecting a missing tow in a tow band. The system may include a fiber placement head configured to apply a tow band to a substrate forming a composite layup. The system may further include an infrared heater positioned in front of a compaction roller and being configured to preheat the substrate prior to application of the tow band using the compaction roller. In addition, the system may include an infrared camera mounted to the fiber placement head and configured to generate a real-time thermal image of the composite layup during the application of the tow band to the substrate. The system may also include a display device coupled to the infrared camera for displaying the real-time thermal image of the composite layup.

Also disclosed is a method of detecting a missing tow in a composite layup. The method may include preheating a substrate prior to applying a tow band on the substrate, and applying the tow band to the substrate to form a composite layup. The method may additionally include generating a real-time thermal image of the composite layup while the tow band is being applied to the substrate, and determining whether a tow is missing based upon the real-time thermal image.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
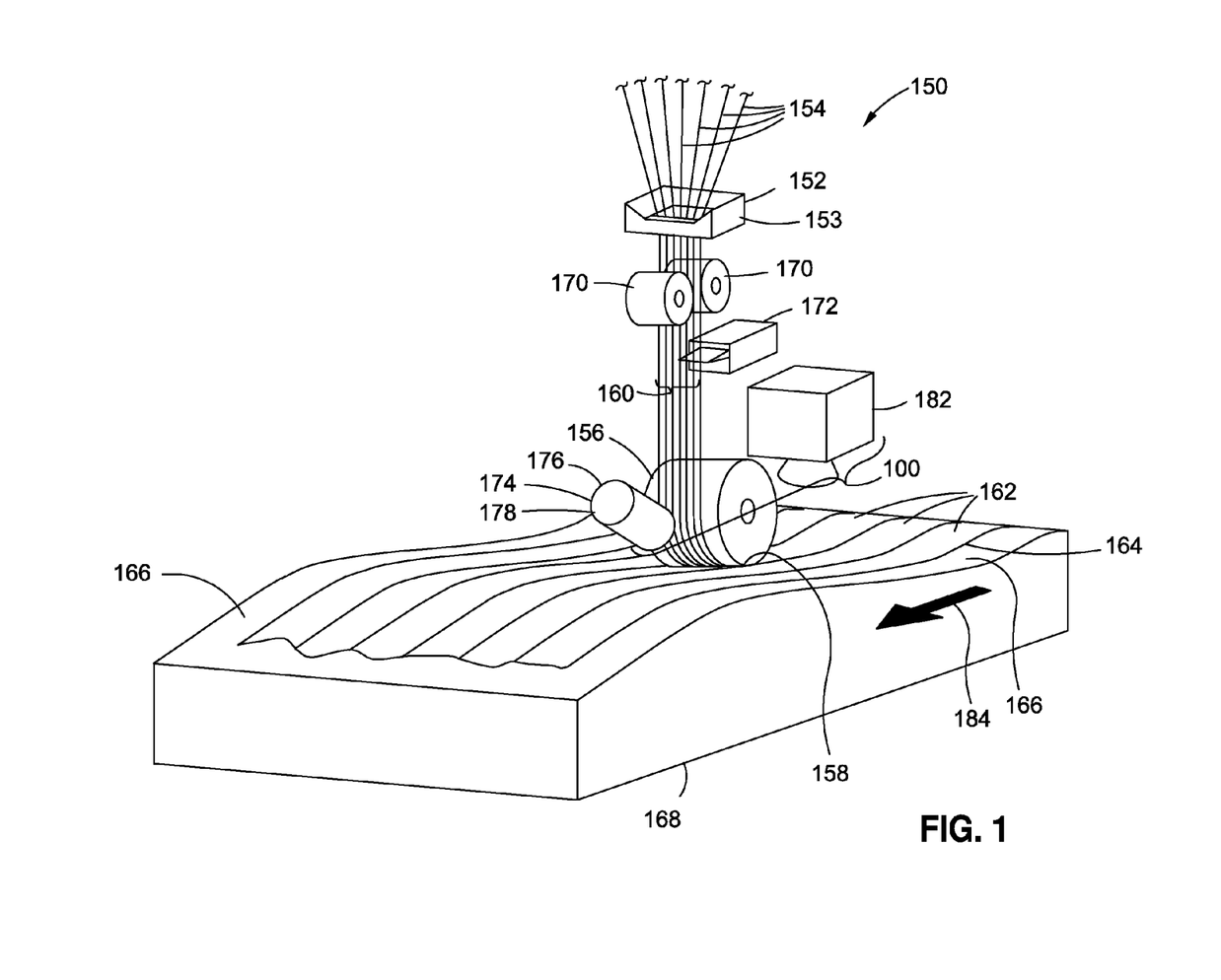
FIG. 1 is a perspective view of an automated fiber placement machine applying a tow band to a tool to form a composite layup.

Referring now to the drawings wherein the showings are for purposes of illustrating various embodiments of the present disclosure, shown in FIG. 1 is a perspective view of a tow detection system 100 for detecting a missing tow 194 (FIG. 4) in a tow band 160. The tow detection system 100 may be implemented in an automated fiber placement machine 150 for applying a prepreg tow band 160 or prepreg composite tape onto a substrate 166 to form a composite layup 164 for a composite part. The substrate 166 may comprise a tool surface of a stationary tool 168 or a rotating mandrel (not shown), or the substrate 166 may comprise courses 162 of previously laid tow bands 160. The automated fiber placement machine 150 may include one or more fiber placement heads 152 for applying the tows 154 onto the substrate 166.

Referring to FIG. 1, as indicated above, each one of the tow bands 160 may be comprised of a plurality of individual tows 154. Each one of the tows 154 may be formed as a bundle of resin-coated reinforcement fibers. Each tow 154 may be provided in a relatively small width or diameter such as in the range of from approximately 0.12 to 0.50 inch although larger widths are possible. The tows 154 may be dispensed from one or more spools (not shown) and threaded through a tow collimator 153 for alignment of the tows 154 into a tow band 160 as shown.

The tow band 160 may pass between a pair of tow restart rollers 170 for controlling the stop-and-start movement of the tow band 160 in accordance with a preprogrammed sequence for applying courses 162 onto the substrate 166. The courses 162 may be applied in parallel arrangement to one another as illustrated in FIG. 1. The tow band 160 may also pass through a tow cutter and clamp mechanism 172 which may be configured to cut the tow 154 at the end of each course 162. A new end of a tow band 160 may be pushed by the restart rollers toward a compaction roller 156. The compaction roller 156 may apply the tow band 160 to the substrate 166. The compaction roller 156 may also apply compaction pressure to the tow band 160 to press the tow band 160 onto the substrate 166 as the compaction roller 156 moves along the surface of the tool 168.

In FIG. 1, the fiber placement head 152 may include a heating device 174 for elevating the temperature of the substrate 166. The heating device 174 may be positioned in front of the location where the tow band 160 initially contacts the substrate 166. In this regard, the heating device 174 may be positioned in front of the compaction roller 156 wherein the tow band 160 is compacted against the substrate 166. The front of the roller may be defined relative to a direction of forward motion of the fiber placement head 152.

The heating device 174 may be configured to preheat the substrate 166 surface prior to the tow band 160 contacting the substrate 166. The heat in the substrate 166 may increase the tack or adhesion between the tow band 160 and the substrate 166. By increasing the tack in the tow band 160, the individual tows 154 may be maintained in position on the substrate 166 during the process of laying up a composite part. The heating device 174 may be provided as a radiative heater 176 such as an infrared heater 178 for heating the substrate 166 and/or for preheating the tow band 160 prior to contact of the tow band 160 with the substrate 166. However, the heating device 174 may be provided in alternative configurations such as a forced hot air heater 180.

Figure 2:
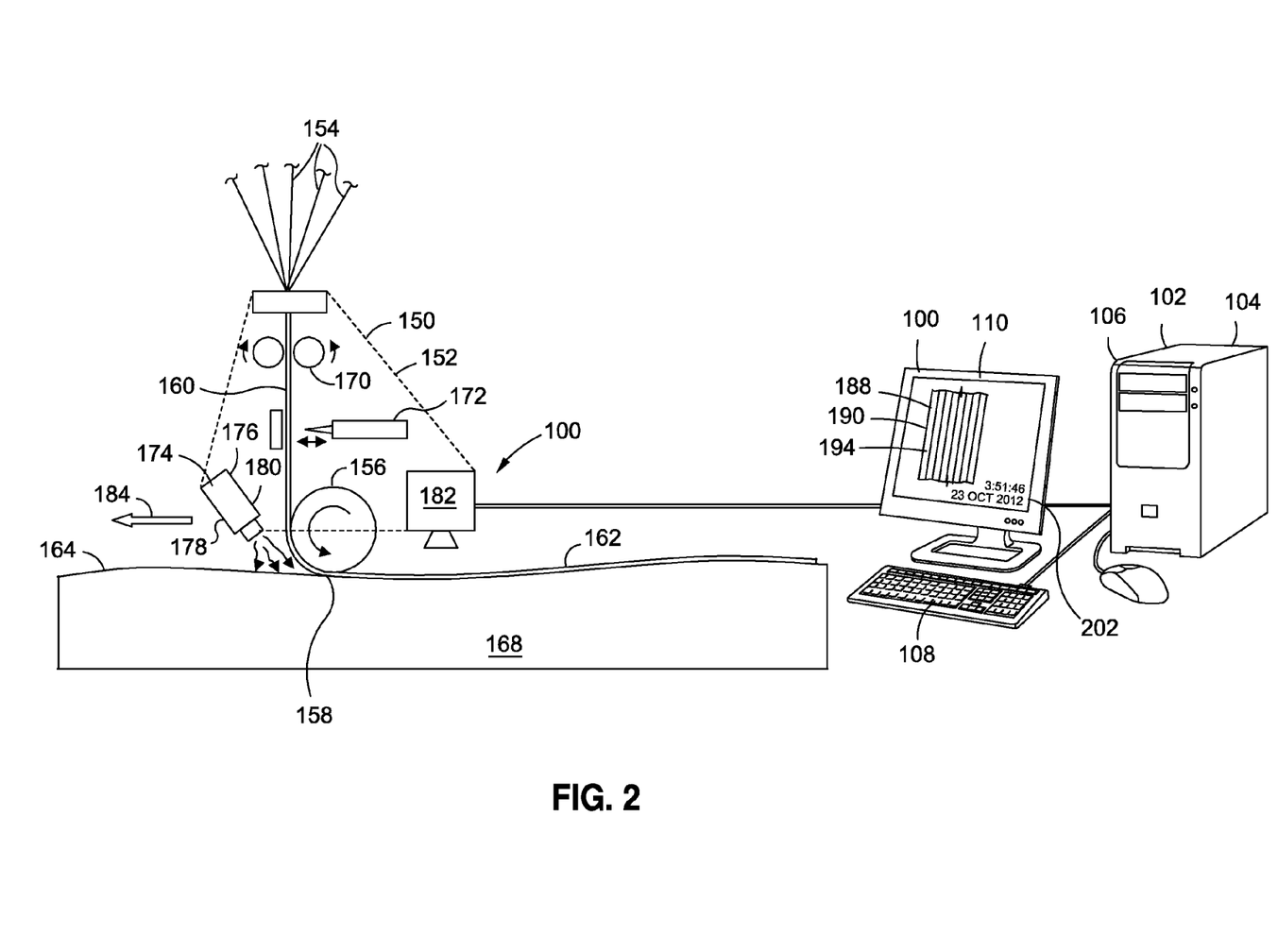
FIG. 2 is a side view of the automated fiber placement machine illustrating an infrared camera positioned behind a compaction roller of the fiber placement head.

Referring to FIGS. 1-2, the automated fiber placement machine 150 may include an infrared camera 182. The infrared camera 182 may be mounted to the fiber placement head 152 and may be configured to generate a real-time thermal image 188 of the composite layup 164 during the application of the tow band 160 to the substrate 166. In an embodiment, the infrared camera 182 may be configured to record a real-time thermal image 188 of the composite layup 164 as the fiber placement head 152 moves along the tool 168. In this regard, the infrared camera 182 may be positioned behind a location where the tow band 160 is compacted against the substrate 166. For embodiments of the fiber placement head 152 having a compaction roller 156, the infrared camera 182 may be positioned behind the compaction roller 156 relative to a direction of forward motion of the fiber placement head 152.

In FIG. 2, the infrared camera 182 may be configured to capture a field of view (not shown) of the composite layup 164 in the area where the tow band 160 has been placed by the compaction roller 156. In this manner, the infrared camera 182 may record an image of the tow band 160 as may be heated in response to heating of the substrate 166 by the infrared heater 178. In this regard, the infrared heater 178 may heat tow bands 160 that have been previously applied to the tool 168 surface. The field of view of the infrared camera 182 preferably captures at least a width of a tow band 160. For example, the infrared camera 182 may have a field of view that may capture a substantial majority of a tow band 160 having 32 tows wherein each one of the tows 154 has a tow 154 width of approximately one-half inch or more making for a total tow band 160 width of approximately 8 inches. However, the infrared camera 182 may have a field of view that may capture a tow band width of any size.

The infrared camera 182 may be communicatively coupled to a display device 110 as shown in FIG. 2 for displaying a real-time thermal image 188 of the tow band 160 as the fiber placement head 152 moves along the tool 168. With a relatively large display device 110 such as a monitor having a diagonal dimension of 14 inches, a tow band width of approximately eight (8) inches may be magnified by at least approximately 50 percent which would result in the thermal image of a missing tow 194 being displayed on the display device 110 at a width of approximately 0.75 inch. The display device 110 may be configured for viewing by an operator of the fiber placement machine 150. With a relatively high resolution infrared camera 182 and with magnification of the real-time thermal image 188, detection of a missing tow 194 within a tow band 160 such as by visual inspection (e.g., by the human eye) of the real-time thermal image 188 may reveal a localized difference 192 in the heat signature 190 of the area of the missing tow 194 relative to the remainder of the tow band 160. In this regard, the tow detection system 100 disclosed herein represents a significant improvement relative to conventional methods for detecting missing tows 194.

In FIG. 2, in an embodiment, the infrared camera 182 may be communicatively coupled to a processor 102 (e.g., a computer) to which the display device 110 may also be coupled. The processor 102 may include a user interface 108 such as a keyboard, a graphical user interface, or other device allowing an operator to interface with the processor 102 and/or to control the infrared camera 182 such as for changing a zoom or a field of view of the camera during operation of the automated fiber placement machine 150. In an embodiment, the infrared camera 182 may also be configured to autonomously operate on a continuous, intermittent, or periodic basis during the application of tows 154 to the substrate 166.

In a further embodiment, the user interface 108 may facilitate manual control of the infrared camera 182 by an operator. For example, the user interface 108 may facilitate manipulation or control of the inferred camera such as to start and stop the recording of the real-time thermal image 188 of the composite layup 164 at any point during the application of tow bands 160 to the substrate 166. The processor 102 may also be configured to facilitate manual override of a preprogrammed tow application sequence of the automated fiber placement machine 150. For example, upon the detection of a missing tow 194 by visual observation of the real-time thermal image 188 of the composite layup 164 on the display device 110, an operator may suspend or temporarily halt the operation of the fiber placement machine 150 to allow for the disposition of the missing tow 154.

The processor 102 may include the display device 110 for displaying one or more thermal images of a composite layup 164 to allow an operator to visually observe the real-time thermal images 188 (e.g., video) recorded by the infrared camera 182 such as during operation of the automated fiber placement machine 150. The processor 102 may additionally include a comparator 104 which may be configured to determine whether a tow 154 is missing from the tow band 160 by comparing a heat signature 190 of the composite layup 164 in a real-time thermal image 188 (FIG. 4) to the heat signature 190 of a composite layup 164 in a baseline thermal image 186 (FIG. 3) as described below.

Figure 3:
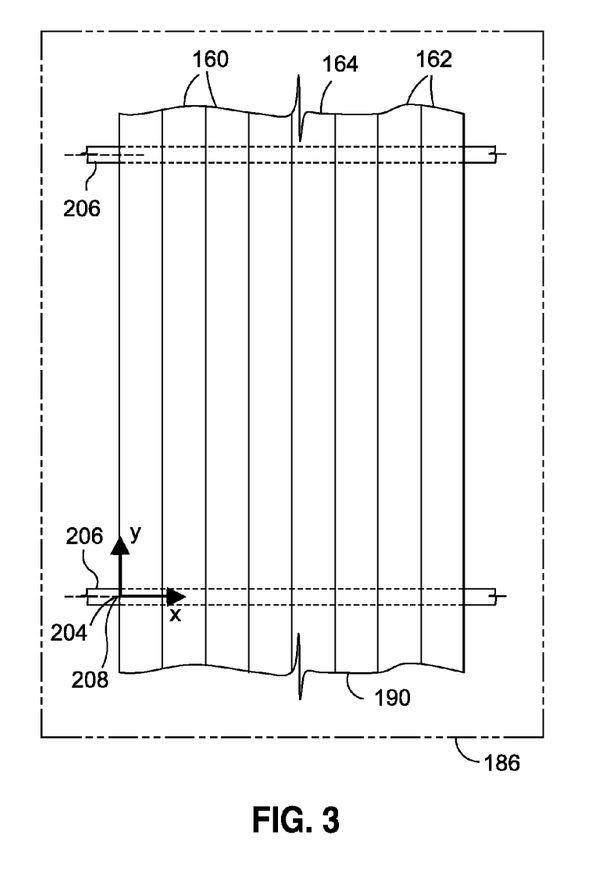
FIG. 3 is an illustration of a baseline thermal image of the composite layup applied by the fiber placement head.
Figure 4:
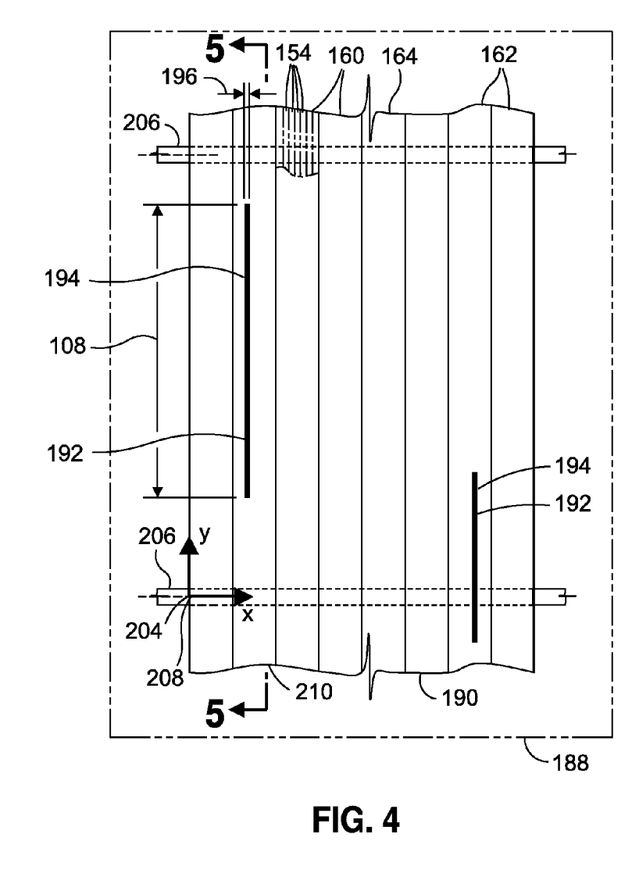
FIG. 4 is an illustration of a real-time thermal image generated by the infrared camera and illustrating a missing tow in one of the tow bands of the composite layup.

Referring to FIGS. 3-4, shown in FIG. 3 is a baseline thermal image 186 of a composite layup 164. Shown in FIG. 4 is a real-time thermal image 188 of a composite layup 164 as may be recorded by an infrared camera 182 mounted behind a compaction roller 156 of a fiber placement head 152. In FIG. 3, the composite layup 164 in the baseline thermal image 186 may have the same configuration as the composite layup 164 being formed on the tool 168 by the fiber placement head 152 and represented by the real-time thermal image 188 of FIG. 4. In an embodiment, the baseline thermal image 186 may represent a composite layup 164 comprised of at least one tow band 160 including tows 154 having the same size, shape, and material configuration and arranged in the same manner (e.g., side-by-side) as at least one tow band 160 in the composite layup 164 represented in the real-time thermal image 188.

In FIGS. 3-4, the comparator 104 may be configured to determine whether a tow 154 is missing from a tow band 160 by comparing a heat signature 190 of the composite layup 164 in the real-time thermal image 188 to the heat signature 190 of a composite layup 164 of the baseline thermal image 186. For example, the composite layup 164 represented in the real-time thermal image 188 in FIG. 4 may include a missing tow. In the real-time thermal image 188, the missing tow 194 may be represented as a localized difference 192 in the heat signature 190 in the area of the missing tow 194 relative to the heat signature 190 of the remainder of the same tow band 160. The difference in the heat signature 190 in the area of the missing tow 194 may occur as a result of a greater amount of heat from underlying substrate 166 (e.g., tool 168 surface or previously-applied tow) radiating upwardly through the gap in the tow band 160 due to the missing tow 194, relative to the amount of heat radiated upwardly through the tows 154 on opposite sides (i.e., lengthwise edges) of the missing tow 194.

For example, in a baseline thermal image 186 of a composite layup 164, each one of the tow bands 160 may have a generally uniform color or shade (e g, uniformly black) which may represent substantially uniform heat radiation upwardly through the tow bands 160 from the underlying substrate 166. In a real-time thermal image 188 of the composite layup 164, a tow band 160 having a missing tow 194 may have a non-uniform color or shade. More specifically, the region of a missing tow 194 may appear lighter in color or shade such as gray shade relative to the remaining portions of the tow band 160 which may appear uniformly black in the real-time thermal image 188 recorded by the infrared camera 182.

FIG. 4 illustrates a localized difference 192 in the heat signature 190 of the tow band 160 in the area of the missing tows 194. Each missing tow 194 has a missing tow length 198, and a missing tow width 196. The missing tow width 196 is equivalent to the width of the remaining tows 154 of the tow band 160. As indicated above, with a resolution of currently-available infrared cameras 182, the missing tow 194 may be detectable in the real-time thermal image 188 by visual observation with the human eye due to the localized difference 192 in the heat signature 190 as indicated above. Manual detection by the human line may also be facilitated by magnification of the real-time thermal image 188 recorded by the infrared camera 182 as mentioned above.

In FIG. 4, the processor 102 may be configured to identify a location and/or position of a missing tow 194 such as by reference to a reference point 204 of the composite layup 164. For example, the reference point 204 may comprise a predetermined longitudinal and/or lateral location of a reference coordinate system 208 100 associated with a tow laydown program 106. The tow laydown program 106 may comprise a computer program such as a numerical control (NC) program having computer-readable instructions for controlling the operation of the automated fiber placement machine 150 for applying courses 162 of tow band 160 to a substrate 166. In an embodiment, the tow laydown program 106 may comprise a NC program for operation of the fiber placement head 152. The processor 102 may be configured to identify a location of the opposite ends of the missing tow 194 with regard to the reference point 204 associated with the NC program. In an embodiment, the reference point 204 may comprise a structural feature 206 that may be associated with the composite layup 164. For example, in a composite layup 164 over a mandrel for generating a skin panel of a barrel section of a fuselage, the location of a missing tow 194 in the composite layup 164 may be identified relative to a stringer or a frame station over which the skin panel may be applied. In this regard, the processor 102 may be configured to index the location of a missing tow 194 relative to a tow laydown program 106.

Figure 5:
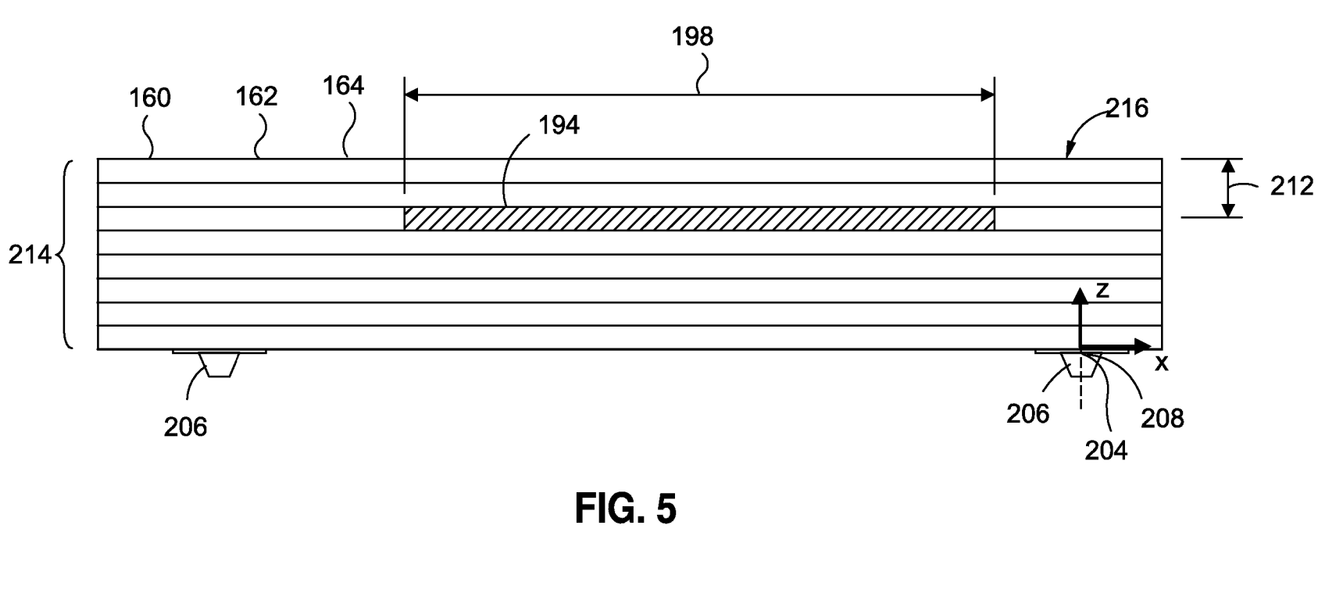
FIG. 5 is a side sectional view of the composite layup illustrating a missing tow band positioned at a ply depth within the composite laminate.

Referring to FIG. 5, shown is a side sectional view of the composite layup 164 illustrating a missing tow band 160 of FIG. 4 and wherein the missing tow band 160 is positioned at a ply depth 212 within the composite layup 164. In an embodiment, the infrared camera 182 may be configured to record a time stamp 202 (FIG. 2) with a real-time thermal image 188 recorded by the infrared camera 182. In this regard, the infrared camera 182 may be configured to continuously record the time during the recording of real-time thermal images 188 of the composite layup 164. In an embodiment, the time stamp 202 may be displayed on the display device 110 along with the real-time thermal image 188 of the composite layup 164. When a missing tow 194 is detected, the processor 102 may be configured to correlate the time stamp 202 to a ply depth 212. In an embodiment, the ply depth 212 may be defined with regard to the location of the ply below the surface of a ply stack 214. The ply stack 214 may be defined by a stacking sequence 200 associated with an NC program for controlling the fiber placement head 152.

In the event that a depression caused by a missing tow 194 is detected in the composite layup 164 surface at a later point during the layup process, a video of a recording of the real-time thermal images 188 can be reviewed to determine the point in time (i.e., the time stamp 202) during the layup sequence when the tow 194 became missing. The time stamp 202 (FIG. 2) can be correlated to the ply position in the stacking sequence 200 associated with an NC program. Rework may be performed by adding an overlay of tows 154 onto the composite layup 164 surface in the area of the missing tow 194 without removing existing ply material and performing an interlaminar repair.

As indicated earlier, the processor 102 may be configured to identify a longitudinal position (not show) and/or a lateral position (e.g., a course location 210—FIG. 4) of the missing tow 194 in the composite layup 164 corresponding to the ply depth 212 of the missing tow 194. For example, during the lay-up of a barrel section of a fuselage, a time stamp 202 on a real-time thermal image 188 of a missing tow 194 may indicate a ply sequence 216 and a position of the missing tow 194 on the barrel section. In this manner, the processor 102 provides a means for accurately identify the location of a missing tow and which may reduce the amount of rework on a composite layup 164 relative to the amount of rework required using conventional method for detecting missing tows. As indicated above, such rework may require removal of one or more of the composite plies overlaying the region of the missing tow 194, and replacing the plies with a composite patch to bring the area of the missing tow 194 to within design tolerances.

Figure 6:
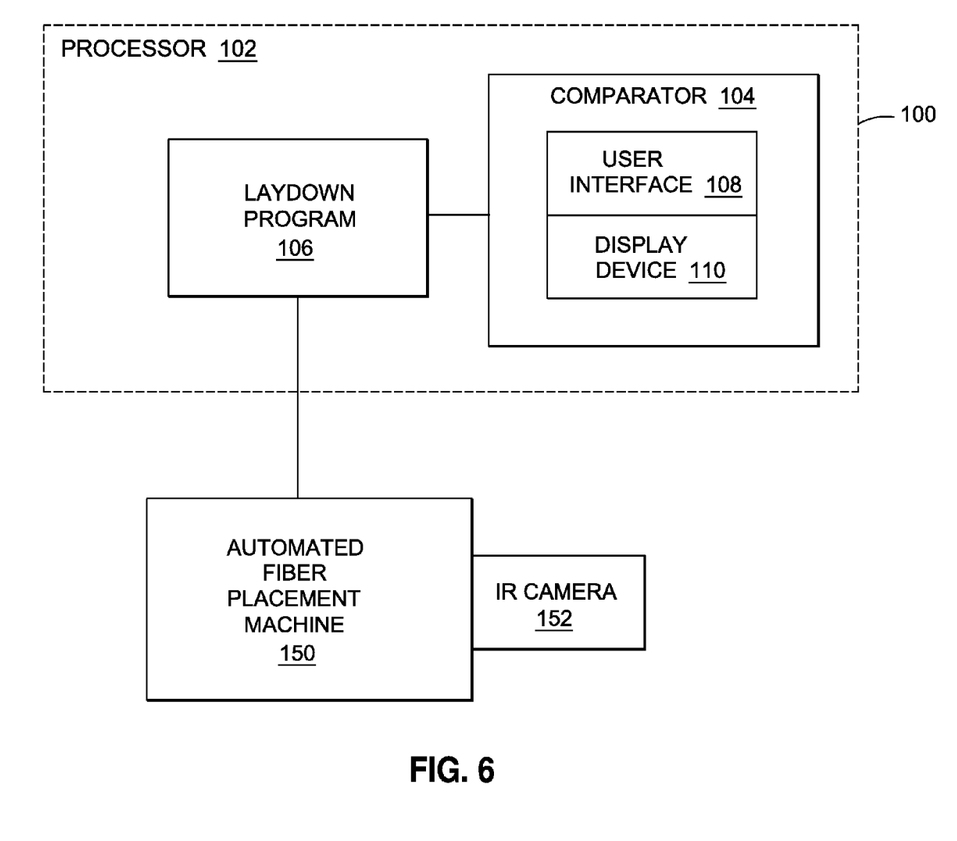
FIG. 6 is a block diagram illustrating a tow detection system.

Referring to FIG. 6, shown is a block diagram of a tow detection system 100 for detecting missing tows 194 in a composite layup 164 such as on an automated fiber placement machine 150. In FIG. 6, the automated fiber placement machine 150 may include the infrared camera 182 as indicated above for recording real-time thermal images 188 of a tow band 160 applied to a substrate 166 by the fiber placement head 152. The automated fiber placement machine 150 may be controlled by a tow laydown program 106 stored on a storage device (not shown) and communicatively coupled to the processor 102 for controlling the operation of the fiber placement head 152. The processor 102 may include a comparator 104 for comparing the real-time thermal image 188 of the composite layup 164 to a baseline thermal image 186 of the composite layup 164 as described above. The real-time thermal image 188 may be displayed on a display device 110 along with an optional time stamp 202 as shown in FIG. 2. The processor 102 may include a user interface 108 for controlling the operation of the infrared camera and/or the operation of the fiber placement machine 150.

Figure 7:
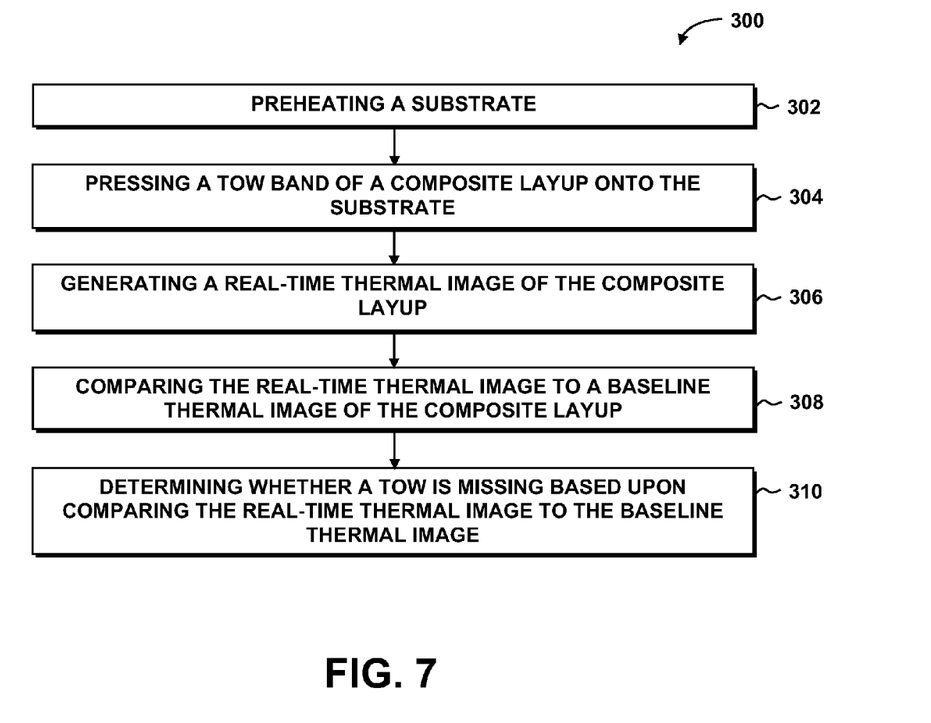
FIG. 7 is a flow diagram having one or more operations that may be included in a method of detecting a missing tow.

Referring to FIG. 7, shown is a flow diagram illustrating one or more operations that may be included in an embodiment of a method 300 of detecting a missing tow 194 in a tow band 160. The method may also be implemented for detecting a missing tape in a tape laying operation.

Step 302 of the method 300 of FIG. 7 may include comprising preheating a substrate 166 at a location in front of a point 158 where the tow 154 is applied to the substrate 166. For example, the preheating may occur and the location directly in front of a compaction roller 156 of a fiber placement head 152. Step 302 may include preheating the substrate 166 using a radiative heater 176 such as an infrared heater 178 for heating the resin. The method may include preheating the substrate 166 prior to applying a tow band 160 of a composite layup 164 on the substrate 166 to improve the tack of the tow band 160. The substrate 166 may comprise the surface of a tool 168 or the substrate 166 may comprise previously-applied tow bands 160.

Step 304 of the method 300 of FIG. 7 may include applying the tow band 160 to the substrate 166. In this regard, the method may include applying the tow band 160 using a fiber placement head 152. For example, the tow band 160 may be applied to the substrate 166 by pressing or compacting the tow band 160 against the substrate 166 with a compaction roller 156 as shown in FIG. 2. In this regard, the compaction roller 156 may facilitate partial consolidation of the composite layup 164.

Step 306 of the method 300 of FIG. 7 may include generating a real-time thermal image 188 of the composite layup 164 while the tow band 160 is being applied to the substrate 166. In an embodiment, the method may include generating the real-time thermal image 188 using an infrared camera 182. In this regard, the method may include positioning an infrared camera 182 behind a point 158 where the tow 154 is applied to the substrate 166. For example, Step 306 may include positioning an infrared camera 182 behind a compaction roller 156 of a fiber placement head 152 relative to a direction of head movement 184. The method may include generating the real-time thermal image 188 while moving the fiber placement head 152 along a direction of head movement 184. The infrared camera 182 may be configured to record or generate real-time thermal images 188 on a continuous basis or on an intermittent or manually-commanded basis as mentioned above.

In an embodiment, the method may include displaying the real-time thermal image 188 on a display device 110 coupled to the infrared camera 182. The method may include visually inspecting with the human eye (i.e., manually inspecting), the real-time thermal image 188 of the composite layup 164 for a localized difference 192 in the heat signature 190 within a tow band 160 which may be representative of a missing tow 194 as mentioned above with regard to FIG. 4.

Step 308 of the method 300 of FIG. 7 may include comparing the real-time thermal image 188 to a baseline thermal image 186 of the composite layup 164. For example, the method may include the use of a comparator 104 which may form part of a processor 102 of a computer-based system 100. The comparator 104 may perform a comparative analysis of the real-time thermal image 188 of the composite layup 164 relative to a baseline thermal image 186 of the composite layup 164. In this regard, the method may include automated inspection of the real-time thermal image 188 of the composite layup 164 for a localized difference 192 in the heat signature 190 of the composite layup 164 relative to the heat signature 190 of a composite layup 164 in a baseline thermal image 186.

Step 310 of the method 300 of FIG. 7 may include determining whether a tow 154 is missing from the tow band 160 based upon comparing the real-time thermal image 188 to the baseline thermal image 186. The method may further include determining whether one or more of the tow bands 160 in the composite layup 164 have a substantially uniform heat signature 190 in the real-time thermal image 188. A non-uniform heat signature 190 in the real-time thermal image 188 may be representative of a missing tow 194.

In a further embodiment, the method may include indexing a location of a missing tow 194 relative to a tow laydown program 106. For example, the method may include recording a time stamp 202 when a missing tow 194 is detected, and correlating the time stamp 202 to a position of the missing tow 194 in the composite layup 164. For example, the time stamp 202 may be correlated to a ply depth 212 of the missing tow 194 in the stacking sequence 200 and a lateral or longitudinal position of the missing tow 194 as mentioned above.

Advantageously, the system and method disclosed herein provides a means for detecting a missing tow 194 in a composite layup 164 immediately after the application of the tow band 160 to the substrate 166 which may minimize the amount of composite material that may be applied with a missing tow 194. In this regard, the system and method disclosed herein may provide the option for automatically or manually suspending the operation of the fiber placement head 152 pending the disposition and possible rework as a result of the missing tow 194. Furthermore, the system and method disclosed herein provides a means for accurately identifying the location of a missing tow 194 in a composite layup 164 which may minimize the amount of rework that may otherwise be required.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A system for detecting a missing tow in a tow band, comprising
    a fiber placement head configured to apply a tow band to a substrate to form a composite layup;
    a heating device configured to preheat the substrate prior to application of the tow band using the fiber placement head;
    an infrared camera mounted to the fiber placement head and configured to generate a real-time thermal image of the composite layup during the application of the tow band to the substrate; and
    a comparator communicatively coupled to the infrared camera and comparing a heat signature in an area of the thermal image where a greater amount of heat from an underlying substrate radiates upwardly through a gap in the tow band due to a missing tow relative to the heat signature in the area of the thermal image where a reduced amount of heat radiates upwardly through tows located on opposite sides of the missing tow; and
    a processor configured to identify a location of opposite ends of the missing tow with regard to a reference point associated with a tow laydown program.

2. The system of claim 1, further comprising:
    a display device configured to display the real-time thermal image of the composite layup.

3. The system of claim 1, wherein:
    the infrared camera is positioned behind a compaction roller relative to a direction of forward motion of the fiber placement head.

4. The system of claim 1, wherein:
    the heating device is positioned in front of a compaction roller relative to a direction of forward motion of the fiber placement head.

5. The system of claim 1, wherein:
    the processor is configured to correlate a time stamp to a ply depth in a stacking sequence.

6. A system for detecting a missing tow in a tow band, comprising
    a fiber placement head configured to apply a tow band to a substrate to form a composite layup;
    an infrared heater positioned in front of a compaction roller and being configured to preheat the substrate prior to application of the tow band using the compaction roller;
    an infrared camera mounted to the fiber placement head and configured to generate a real-time thermal image of a composite layup during the application of the tow band to the substrate;
    a display device coupled to the infrared camera and configured to display the real-time thermal image of the composite layup; and
    a comparator communicatively coupled to the infrared camera and comparing a heat signature in an area of the thermal image where a greater amount of heat from an underlying substrate radiates upwardly through a gap in the tow band due to a missing tow relative to the heat signature in the area of the thermal image where a reduced amount of heat radiates upwardly through tows located on opposite sides of the missing tow; and
    a processor configured to identify a location of opposite ends of the missing tow with regard to a reference point associated with a tow laydown program.

7. A method of detecting a missing tow in a tow band, comprising the steps of:
    preheating a substrate;
    applying the tow band to the substrate to form a composite layup;
    generating a real-time thermal image of the composite layup while the tow band is being applied to the substrate;
    comparing a heat signature in an area of the thermal image where a greater amount of heat from an underlying substrate radiates upwardly through a gap in the tow band due to a missing tow relative to the heat signature in the area of the thermal image where a reduced amount of heat radiates upwardly through tows located on opposite sides of the missing tow; and
    identifying a location of opposite ends of a missing tow with regard to a reference point associated with a tow laydown program.

8. The method of claim 7, wherein the step of generating the real-time thermal image:
    generating the real-time thermal image using an infrared camera.

9. The method of claim 8, wherein the step of generating the real-time thermal image comprises:
    generating the real-time thermal image using the infrared camera mounted behind a compaction roller of a fiber placement head.

10. The method of claim 9, wherein the step of generating the real-time thermal image comprises:
    generating the real-time thermal image while moving the fiber placement head along a direction of head movement.

11. The method of claim 7, wherein the step of determining whether a tow is missing comprises:
    visually inspecting, on a display device, the real-time thermal image for a localized difference in a heat signature of the composite layup.

12. The method of claim 11, wherein the step of inspecting the real-time thermal image for a localized difference in the heat signature comprises:
    determining whether the tow band has a substantially uniform heat signature.

13. The method of claim 7, wherein the step of determining whether a tow is missing comprises:
    comparing a heat signature of the real-time thermal image of the composite layup to a heat signature of a baseline thermal image of the composite layup.

14. The method of claim 7, further comprising the steps of:
    recording a time stamp when a missing tow is detected; and correlating the time stamp to a position of the missing tow in the composite layup.

15. The method of claim 14, further comprising the step of:
correlating the time stamp to a ply depth in a stacking sequence.

16. The method of claim 7, wherein the step of preheating the substrate comprises:
preheating the substrate using a heating device configured to heat an area of the substrate directly in front of a point where the tow is applied to the substrate.

17. The method of claim 7, wherein the step of preheating the substrate comprises:
preheating the substrate using at least one of a radiative heater and a forced hot air heater.

* * * * *